US007699606B2

(12) United States Patent
Sachdeva et al.

(10) Patent No.: US 7,699,606 B2
(45) Date of Patent: *Apr. 20, 2010

(54) METHOD AND APPARATUS FOR GENERATING AN ORTHODONTIC TEMPLATE THAT ASSISTS IN PLACEMENT OF ORTHODONTIC APPARATUS

(75) Inventors: Rohit Sachdeva, Plano, TX (US); Rudger Rubbert, Berlin (DE); Thomas Weise, Berlin (DE); Friedrich Riemeier, Berlin (DE); Michael Placke, Plano, TX (US); Mathew Johnson, Dallas, TX (US)

(73) Assignee: Orametrix, Inc., Richardson, TX (US)

( * ) Notice: Subject to any disclaimer, the term of this patent is extended or adjusted under 35 U.S.C. 154(b) by 850 days.

This patent is subject to a terminal disclaimer.

(21) Appl. No.: 11/135,143

(22) Filed: May 23, 2005

(65) Prior Publication Data

US 2005/0208450 A1  Sep. 22, 2005

Related U.S. Application Data

(63) Continuation of application No. 10/414,542, filed on Apr. 14, 2003, now Pat. No. 6,918,761, which is a continuation of application No. 09/560,127, filed on Apr. 28, 2000, now Pat. No. 6,554,613, which is a continuation-in-part of application No. 09/552,190, filed on Apr. 19, 2000, now abandoned.

(51) Int. Cl.
*A61C 3/00* (2006.01)

(52) U.S. Cl. ........................................................ 433/24
(58) Field of Classification Search .................. 433/3, 433/8, 24
See application file for complete search history.

(56) References Cited

U.S. PATENT DOCUMENTS

| 6,123,544 | A  | * | 9/2000 | Cleary ......................... 433/24 |
| 6,554,613 | B1 | * | 4/2003 | Sachdeva et al. .............. 433/24 |
| 6,918,761 | B2 | * | 7/2005 | Sachdeva et al. .............. 433/24 |

* cited by examiner

*Primary Examiner*—Ralph A Lewis
(74) *Attorney, Agent, or Firm*—McDonnell Boehnen Hulbert & Berghoff LLP

(57) ABSTRACT

A method and apparatus for generating a orthodontic template that assists in the placement of an orthodontic apparatus includes processing that begins by obtaining a digital model of an orthodontic structure of an orthodontic patient. The processing continues by obtaining a selection of one of a plurality of orthodontic apparatuses for the orthodontic structure to produce a selected orthodontic apparatus. The processing then continues by obtaining a digital model of placement of the selected orthodontic apparatus on the digital model of the orthodontic structure. The processing then continues by retrieving a digital image of a tooth mounting apparatus (e.g., a bracket, a band, a headgear tube, etc.) of the selected apparatus for a given tooth. The processing then continues by generating a orthodontic template for holding a physical embodiment of the tooth mounting apparatus based on the digital image of the tooth mounting apparatus, the digital model of the placement, and at least a portion of the digital model of the orthodontic structure.

29 Claims, 13 Drawing Sheets

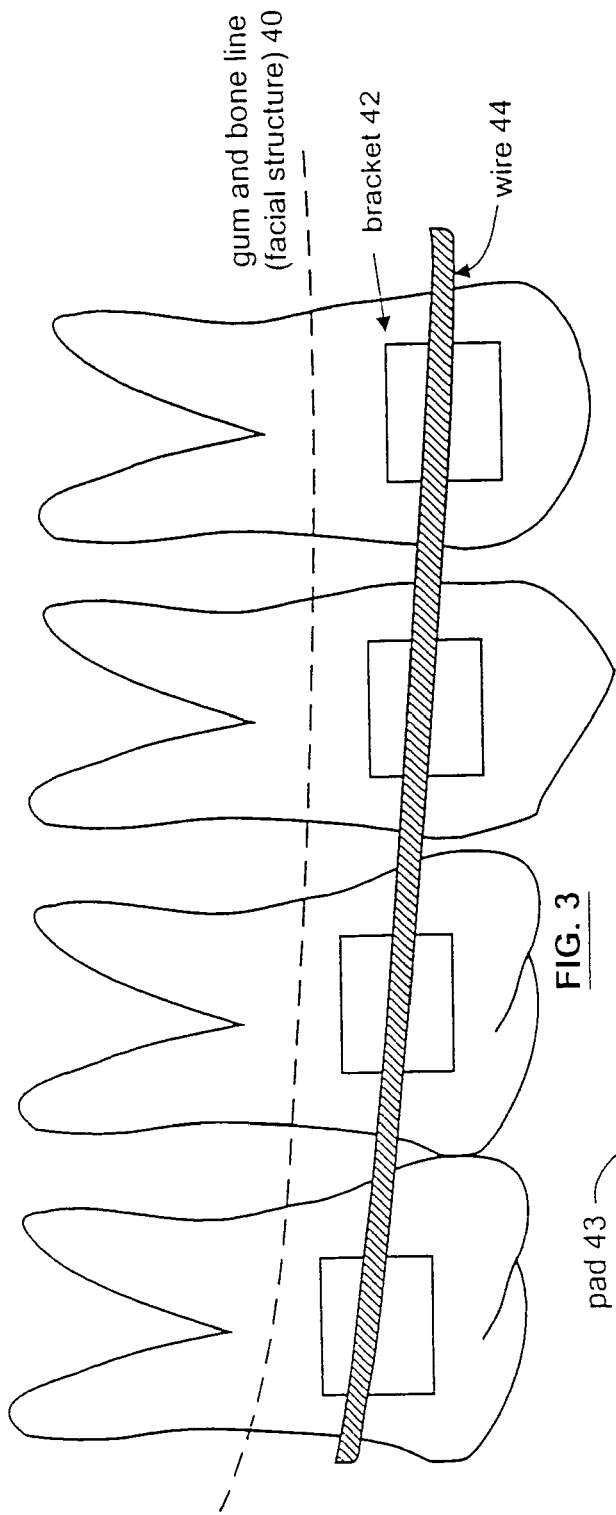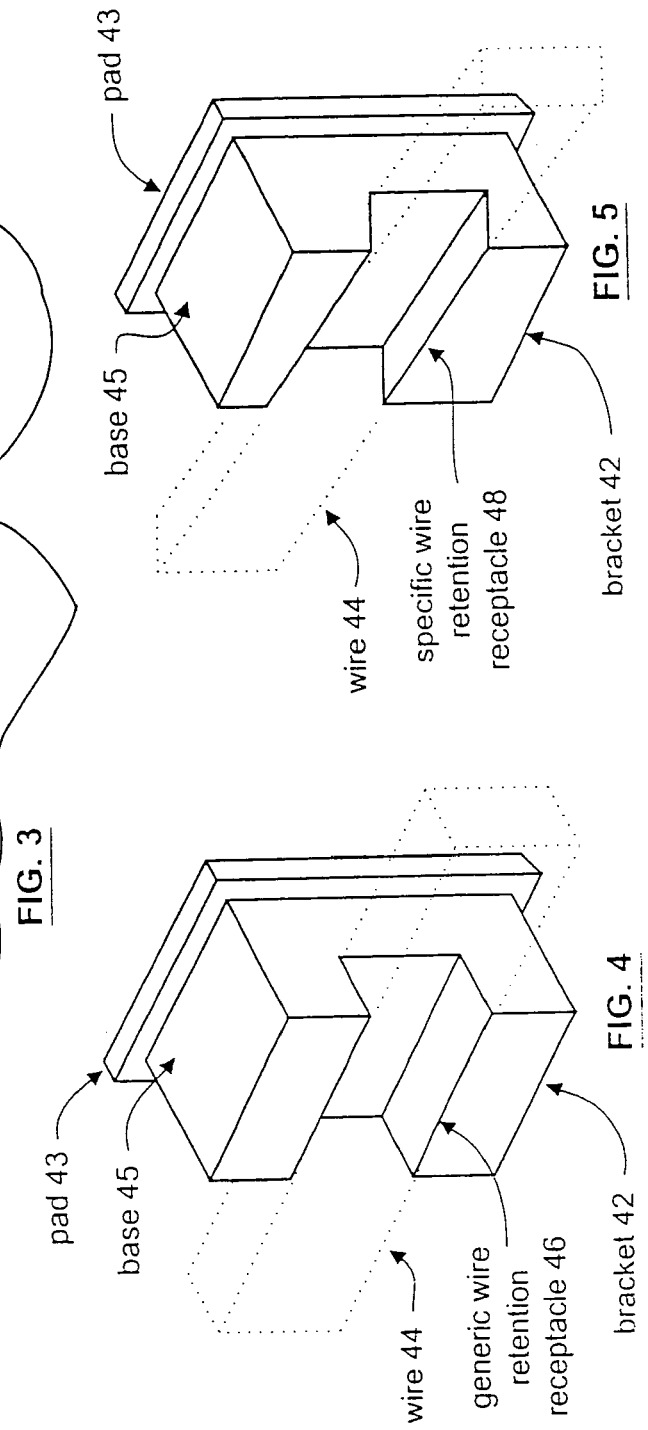

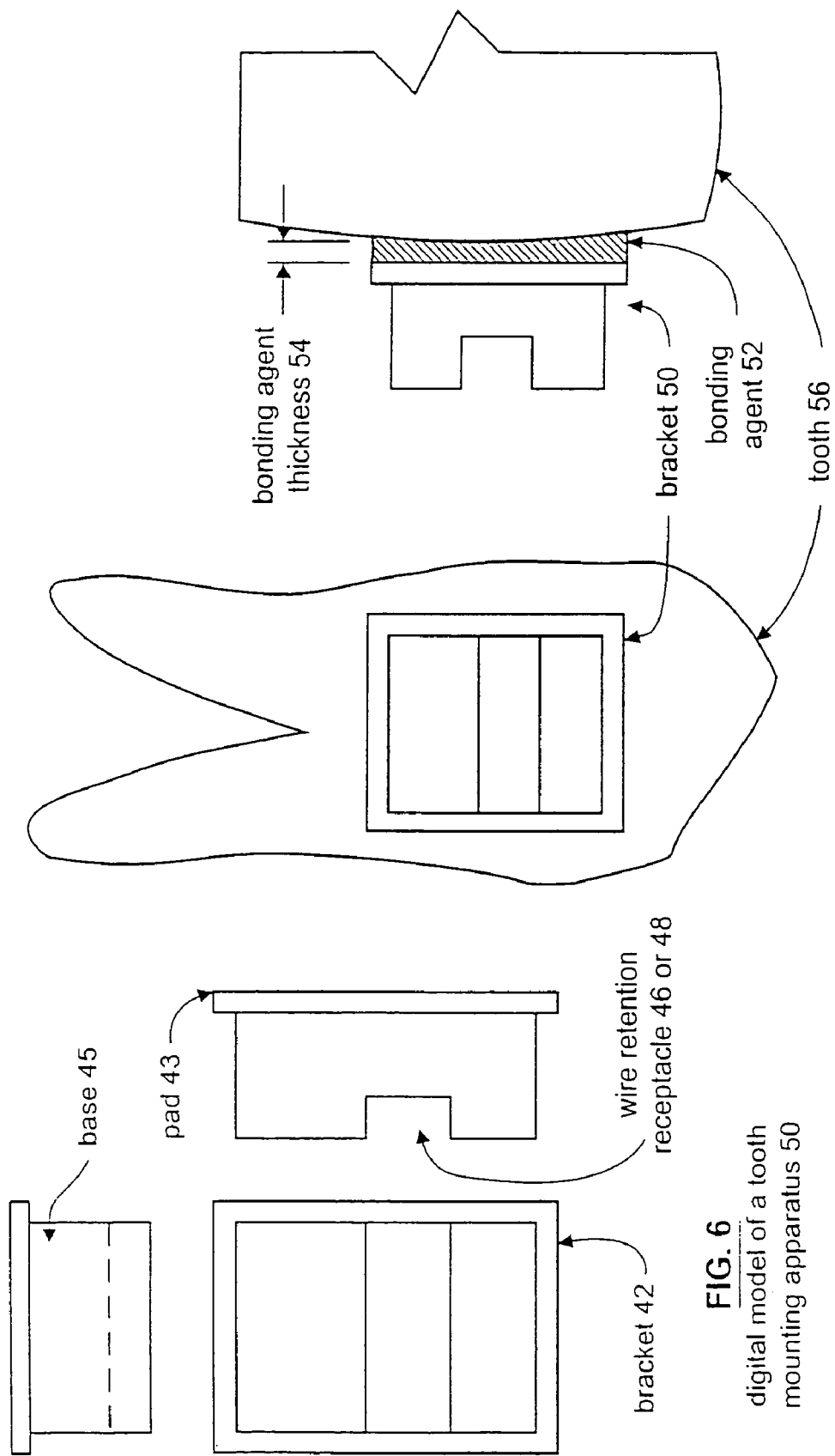

METHOD AND APPARATUS FOR GENERATING AN ORTHODONTIC TEMPLATE THAT ASSISTS IN PLACEMENT OF ORTHODONTIC APPARATUS

CROSS-REFERENCE TO RELATED APPLICATIONS

This is a continuation application of prior application Ser. No. 10/414,542, filed Apr. 14, 2003, now U.S. Pat. No. 6,918, 761, which is a continuation of application Ser. No. 09/560, 127 filed Apr. 28, 2000, now U.S. Pat. No. 6,554,613, which is a continuation in part of Ser. No. 09/552,190 filed Apr. 19, 2000, abandoned.

This application is related to application Ser. No. 09/560, 129 filed Apr. 28, 2000, now U.S. Pat. No. 6,318,995 and Ser. No. 09/560,130, also filed Apr. 28, 2000, now U.S. Pat. No. 6,736,638.

TECHNICAL FIELD OF THE INVENTION

This invention relates generally to the practice of orthodontics and in particular to a method and apparatus for generating an orthodontic template for placing orthodontic apparatus.

BACKGROUND OF THE INVENTION

Orthodontics is known to be the practice of manipulating a patient's teeth to provide better function and appearance. In general, brackets are bonded to a patient's teeth and coupled together with an arch wire. The combination of the brackets and wire provide a force on the teeth causing them to move. Once the teeth move to a desired location and are held in place for a certain period of time, the body adapts bone and tissue to maintain the teeth in the desired location. To further assist in retaining the teeth in the desired, the patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his or her expertise to place the brackets and/or bands on the teeth and then manually bends(i.e., shape) the arch wire such that a force is asserted on the teeth to reposition the teeth into the desired physical orthodontic structure. As the teeth move towards the desired location, the orthodontist makes continual judgments as to the progress in the treatment, the next step in the treatment (e.g., new bends in the arch wire, repositioning or replacing brackets, is headgear required, etc.) and the success of the previous step.

In general, the orthodontist makes manual adjustments to the arch wire and/or replaces or repositions brackets based on his or her own expert opinion. Unfortunately, in the oral environment, it is impossible for a human being to accurately develop a three-dimensional mental image of an orthodontic structure due to the limitations of human site and the physical structure of a human mouth. In addition, it is humanly impossible to accurately estimate three-dimensional wire bends (with an accuracy within a few degrees and to manually apply such bends to a wire). Further it is humanly impossible to determine an ideal bracket location to achieve the desired orthodontic structure based on mental images. It is also extremely difficult to manually place brackets in the estimated ideal location. Accordingly, orthodontic treatment is an iterative process requiring multiple wire changes, with the type, success, and speed of treatment being very much dependent on the orthodontist's motor skills and diagnostic expertise. As a result of multiple wire changes, patient discomfort is increased as well as treatment costs. As one would expect, the quality of care varies greatly from orthodontist to orthodontist, as does the time to treat a patient.

As described, the practice of orthodontic is very much an art, relying on the expert opinion and judgment of the orthodontist. In an effort to shift the practice of the orthodontic from an art to a science, many innovations have been developed. For example, U.S. Pat. No. 5,518,397 issued to Andreiko, et. al, provides a method of forming an orthodontic brace. Such a method includes obtaining a model of the teeth of a patient's mouth and a prescription of desired positioning of such teeth. The contour of the teeth of the patient's mouth is determined from the model. Calculations of the contour and the desired positioning of the patient's teeth are then made to determine the geometry (e.g., groves or slots) to be provided. Custom brackets including a special geometry have been created for receiving an arch wire to form an orthodontic brace system. Such geometry is intended to provide for the disposition of the arched wire on the bracket in a progressive curvature of a horizontal plane and a substantially linear configuration in a vertical plane. The geometry of the bracket is altered, (e.g., by cutting groves into the bracket at individual positions and angles and with particular depth) and in accordance with such calculations of the geometry of the patient's teeth. In such a system, the brackets are customized to provide three-dimensional movement of the teeth once the wire, which has a two-dimensional shape, (i.e., linear shape in the vertical plane and curvature in the horizontal plane) is applied to the brackets.

Unfortunately, the current innovations to change the practice of orthodontics from an art to a science have only made limited progress. This is due to, but not restricted to, the brackets being the focal point for orthodontic manipulation. By having the brackets as the focal point, placement of each bracket on a corresponding tooth is critical. Since each bracket includes a custom sized and positioned wire retaining grove, a misplacement of a bracket by a small amount (e.g., an error vector having a magnitude of a millimeter or less and an angle of a few degrees or less) can cause a different forced system (i.e., magnitude of movement and direction of movement) than the desired force system to be applied to the teeth. As such, the tooth will not be repositioned to the desired location.

In general, there are two methods for applying brackets to teeth: an indirect method and a direct method. For the indirect method, a tooth impression model is created in the patient's mouth using a hardening material. The tooth impression model is then used to create a model of the teeth. Brackets are then manually placed on, and temporarily bonded to, the model of the teeth. A transfer tray is then fabricated by taking an impression of the model of the teeth with the brackets installed. Once the transfer tray is fabricated, brackets are placed therein and a bonding agent is applied to the bonding pad of each bracket.

Once an orthodontist has a transfer tray with brackets installed, the orthodontist manually positions the tray into the patient's mouth to place the brackets on the patient's teeth. Once the orthodontist believes the brackets are positioned properly, (s)he bonds the brackets to the teeth. Unfortunately, this manual process has limited accuracy to due human limitations. As such, it is extremely difficult, if not impossible, for the orthodontist to position all of the brackets in an ideal location with known bonding agent thickness, slot position, etc. or verify such placements.

The direct bonding method is, as the name implies, a method where the brackets are directly bonded to the patient's teeth without the use of a transfer tray. The direct bonding method is typically less accurate than the indirect bonding method since the entire process is done manually without any mechanical assistance. Furthermore, it is difficult to manually judge the location of brackets during placement.

U.S. Pat. No. 5,368,478 issued to Andreiko, et. al provides an indirect bonding method that forms jigs for custom placement of orthodontic appliances on teeth. In general, the '478 patent teaches that each orthodontic template is provided with a surface conforming to the contour of the tooth to which they are to be mounted. Another surface of the orthodontic template engages the bracket to hold it in the proper position and orientation for mounting to the tooth and spaced in relation to the contour surface to precisely locate the orthodontic template on the tooth. The orthodontic templates are particularly useful in positioning brackets of custom appliances desired to the individual anatomy of the patient and requiring custom positions of the brackets on the teeth. While the '478 patent discloses a method for forming a jig, such jig utilization still keeps the bracket as the focal point of the orthodontic treatment. U.S. Pat. Nos. 5,011,405 and 5,542,842 teach indirect bonding approaches, but suffer the same limitations as the '478 patent.

Therefore, a need exists for a method and apparatus for generating an orthodontic template that assists in the placement of an orthodontic apparatus without the limitations of current jig and transfer tray designs.

BRIEF DESCRIPTIONS OF THE DRAWINGS

FIG. 3 illustrates a graphical representation of an orthodontic apparatus applied to teeth in accordance with the present invention;

FIG. 4 illustrates an isometric view of a bracket having a generic wire retention receptacle in accordance with the present invention;

FIG. 5 illustrates an isometric view of a bracket including a specific wire retention receptacle in accordance with the present invention;

FIG. 6 illustrates a three-dimensional digital model of a tooth mounting apparatus in accordance with the present invention;

FIG. 7 illustrates a graphical representation of a three-dimensional model of a bracket, or tooth mounting apparatus, being applied to a tooth in accordance with the present invention;

DETAILED DESCRIPTION OF A PREFERRED EMBODIMENT

Generally, the present invention provides a method and apparatus for generating a orthodontic template that assists in the placement of an orthodontic apparatus. Such a method and apparatus includes processing that begins by obtaining a digital model of an orthodontic structure of an orthodontic patient. Such a model may be obtained in accordance with patent application, which is hereby incorporated herein by reference, entitled "Method and Apparatus for Producing a Three-Dimensional Digital Model of an Orthodontic Patient" having a filing date of Nov. 30, 1999 and a Ser. No. 09/452,034, now abandoned. The processing continues by obtaining a selection of one of a plurality of orthodontic apparatuses for the orthodontic structure to produce a selected orthodontic apparatus. The plurality of orthodontic apparatuses may be stored in a database and designed in accordance with patent application, which is hereby incorporated herein by reference, entitled "Method and Apparatus for Designing an Orthodontic Apparatus to Provide Tooth Movement" having a filing date of Nov. 30, 1999 and having a Ser. No. 09/451,564, now U.S. Pat. No. 6,350,120. The processing then continues by obtaining a digital model of placement of the selected orthodontic apparatus on the digital model of the orthodontic structure. The processing then continues by retrieving a digital image of a tooth mounting apparatus (e.g., a bracket, a band, a head gear tube, etc:) of the selected apparatus for a given tooth. The processing then continues by generating a orthodontic template for holding a physical embodiment of the tooth mounting apparatus based on the digital image of the tooth mounting apparatus, the digital model of the placement, and at least a portion of the digital model of the orthodontic structure. With such a method and apparatus, an orthodontic template may be designed without the bracket being the focal point of orthodontic manipulation and thus avoiding the limitations of prior art embodiments. As such, the present invention offers, among other advantages, the ability to iteratively and interactively simulate dynamic/static orthodontic process to optimize bracket placement and the corresponding design of the orthodontic template; the ability to have the orthodontist manufacture the orthodontic template or a portion thereof the ability to select material characteristics for the template; and the ability to allow the orthodontist to select any orthodontic apparatus and to accurately make an orthodontic structure for the selected orthodontic apparatus and the given patient.

Figure 1:
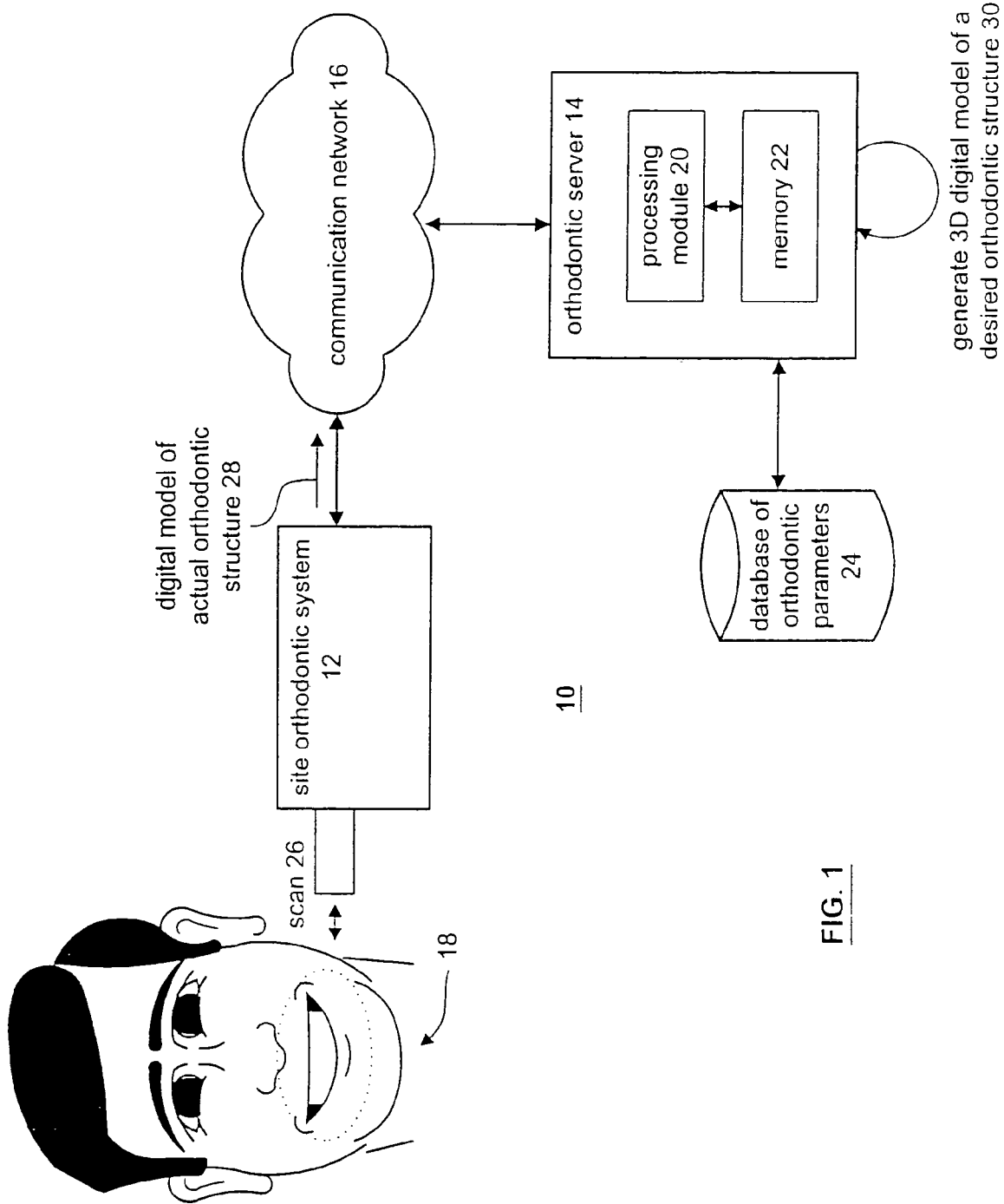
FIG. 1 illustrates a schematic block diagram of an orthodontic service system in accordance with the present invention.
Figure 2A:
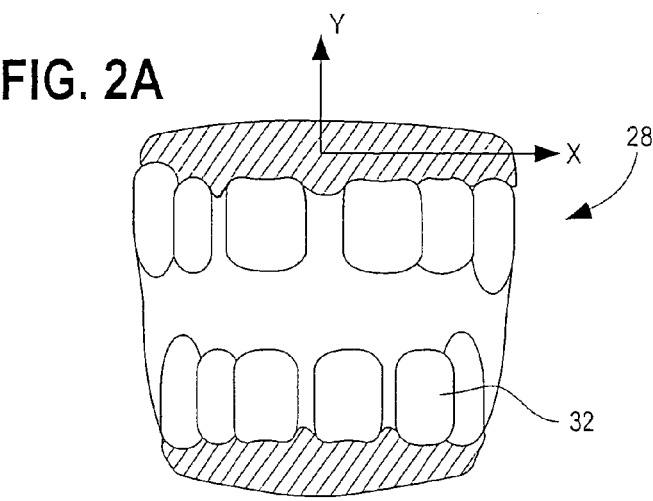
FIGS. 2A-2E illustrate a graphical representation of a three-dimensional digital model of an actual orthodontic structure in accordance with the present invention.
Figure 2B:
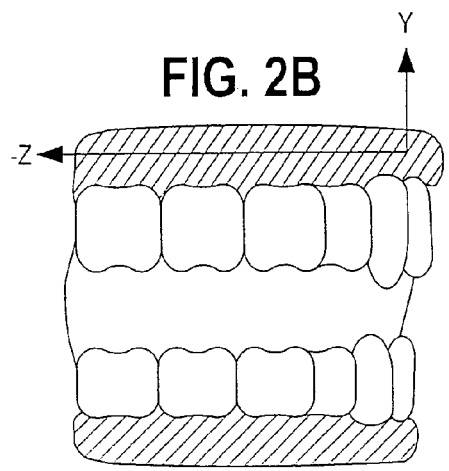
Figure 2C:
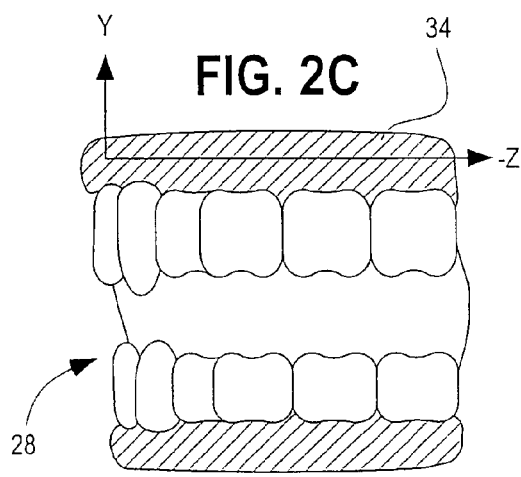
Figure 2D:
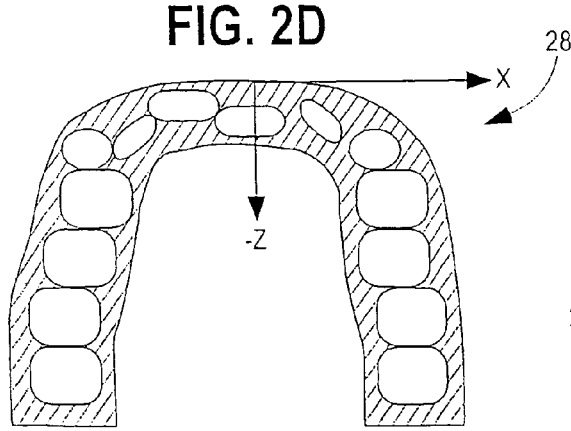
Figure 2E:
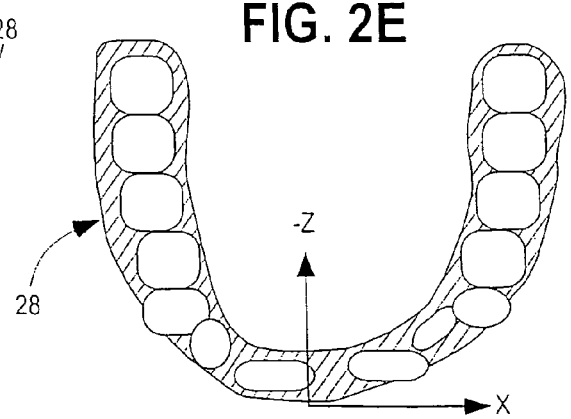

The present invention can be more fully described with FIGS. 1 through 12. FIG. 1 illustrates a schematic block diagram of an orthodontic servicing system 10 that includes a site orthodontic system 12, an orthodontic server 14, a communication network 16, and a database of orthodontic parameters 24. In operation, the site orthodontic system 12 scans 26 the patient's 18 orthodontic structure (i.e., teeth, gums, lips, upper and lower arches, and/or other facial features). The site orthodontic system 12 converts the scanned images of the orthodontic structure of the patient to use a digital model of the actual orthodontic structure 28. The orthodontic server 14 receives the digital model of the actual orthodontic structure 28 via the communication network 16. The communication network 16 may be a direct connect, the internet, local area network, wide area network, wide area network, and/or any device that enables the transference of digital information from one computing type system to another. Note that a specific embodiment of three-dimensional scanning is described in patent application Ser. No. 09/560,584, filed before the United States Patent Office on Apr. 28, 2000, now issued as U.S. Pat. No. 7,068,836, and is hereby incorporated herein by reference.

The orthodontic server includes a processing module 20 and memory 22. The processing module 20 may be a single processing device or a plurality of processing devices. Such a processing device may be a microprocessor, microcomputer, microcontroller, digital signal processor, central processing unit, state machine, logic circuitry, and/or any device that manipulates signals (e.g., analog and/or digital) based on operational instructions. The memory 22 may be a single memory device or a plurality of memory devices. Such a memory device may be a read-only memory, random access memory, floppy disk memory, hard drive memory, system memory, flash memory, and/or any device that stores digital information. Note that when the processing model 20 implements one or more of its functions via a state machine or logic circuitry, the memory storing the corresponding operational instructions is embedded within the circuitry comprising the state machine and/or logic circuitry.

The orthodontic server 14 generates a three-dimensional digital model of the desired orthodontic structure 30 from the digital model of the actual orthodontic structure 28 and orthodontic parameters contained in the database of orthodontic parameters 24. To achieve this, the processing module 20 via operational instructions stored in memory 22, performs the processing steps which are discussed in greater detail in patent application, which is hereby incorporated herein by reference, entitled "Method and Apparatus for Generating a Desired Three-Dimensional Digital Model of an Orthodontic Structure" having a filing date of Nov. 30, 1999 and a Ser. No. of 09/452,031, now U.S. Pat. No. 6,431,870. For a more detailed discussion of the site orthodontic system 12, the orthodontic server 14 and the database of orthodontic parameters refer to patent application, which is hereby incorporated herein by reference, entitled "Method and Apparatus for Determining and Monitoring Orthodontic Treatment" having a filing date of Nov. 30, 1999 and a Ser. No. of 09/451,637, now U.S. Pat. No. 6,471,512, patent application, which is hereby incorporated herein by reference, entitled "Method and Apparatus for Treating an Orthodontic Patient" filed on Nov. 30, 1999 having a Ser. No. of 09/451,560, now U.S. Pat. No. 6,540,512, and patent application, which is hereby incorporated herein by reference, entitled "Method and Apparatus for Site Treatment of an Orthodontic Patient" having a filing date of Nov. 30, 1999 and a Ser. No. of 09/452,038, now U.S. Pat. No. 6,315,553.

FIGS. 2A-2E illustrate a graphical representation of the three-dimensional digital model of an actual orthodontic structure 28. As shown, the orthodontic structure is mapped to X, Y, Z coordinate system. For a detailed discussion of the mapping of the digital model to X, Y, Z coordinate system refer to patent application entitled "Method and Apparatus for Producing a Three-Dimensional Digital Model of an Orthodontic Patient" filed on Nov. 30, 1999 and having a Ser. No. of 09/452,034, now abandoned. As shown, the three-dimensional model of the actual orthodontic structure 28 includes surface images of the teeth 32 and gums 34. The three-dimensional model may further include surface images of the bone structure, lips and other soft facial tissues. The generation of the three-dimensional digital model of the actual orthodontic structure is further described in the aforementioned patent application in this paragraph.

FIG. 3 illustrates a graphical representation of a patient's teeth having an orthodontic apparatus attached thereto. The orthodontic apparatus includes a plurality of brackets 42 and an arch wire 44. As shown, the brackets 42 and arch wire 44 are installed below the gum and bone line 40. Throughout the treatment, the brackets are fixed to the teeth whereby the arch wire 44 is manipulated to achieve the desired orthodontic structure (i.e., the desired tooth placement) via an optimized forced system. The brackets 42 may be the type of brackets illustrated in FIGS. 4 and 5.

FIG. 4 illustrates a standard bracket or a generic prescription bracket 42 that includes a generic wire retention receptacle 46, a bonding pad 43, and a base 45. Typically the bonding pad 43 will include a wire mesh and be securely attached to the base 45. For the standard bracket, the generic wire retention receptacle 46 is a simple groove (i.e., a slot) in the bracket 42 without complex angles or depths. For the generic prescription bracket 42, often referred to as a straight arch wire bracket, the generic wire retention receptacle 46 is a groove in the bracket 42 that includes a generic angularity of complex angles and grooves that have been normalized for semi-custom treatment. The arch wire 44 is inserted into the bracket as shown to provide the desired torque or force system on the corresponding tooth.

FIG. 5 illustrates a custom bracket 42 having a specific wire retention receptacle 48, a bonding pad 43, and a base 45. In this embodiment, the bracket has a retention receptacle 48 designed to include complex angles of depth and groove that are determined for a particular patient. As such, the orthodontic apparatus applied to a patient's tooth may include brackets having generic arch wire retention receptacles 46 or brackets having specific wire retention receptacles 48.

FIG. 6 illustrates a three-dimensional digital model of a tooth mounting apparatus 50. The tooth mounting apparatus 50 may be a bracket, band, head gear tube, or any device used to mount onto a patient's tooth for reception of a displacement apparatus such as an arch wire and/or head gear. The three-dimensional digital model of the tooth mounting apparatus 50, hereinafter referred to generically as a bracket, may be scanned into the database 24, generated by a computer graphics designer, or transferred from a pre-existing library of the digital images. As shown, the bracket includes a bonding pad, a height, width and depth, and a slot for receiving the arch wire.

FIG. 7 illustrates a graphical representation of a three-dimensional model of a given tooth having a bracket fixed thereto. The tooth 56 has a bracket 50 mounted to it via a bonding agent 52. The bonding agent 52 may be an adhesive, cement, and/or any agent used within orthodontics to adhere a bracket to a tooth. The bracket is offset from the tooth by the bonding agent thickness 54. The particular example of FIG. 7 is generated digitally within the server 14 to simulate the desired tooth movement. Patent application entitled "Method and Apparatus for Simulating Tooth Movement for an Orthodontic Patient" having a filing date of Nov. 30, 1999 and a Ser. No. of 09/451,609, now U.S. Pat. No. 6,250,918 describes the process of digitally determining the force systems on a patient's teeth using brackets, bonding agents thickness, arch wires, etc. to achieve desired results. Once the digital model of a tooth having the bracket positioned thereon in accordance with the desired positioning is derived, an orthodontic template may be generated.

FIGS. 8-12 illustrate various embodiments and/or features of orthodontic templates. But, prior to discussing such embodiments and/or features, a general discussion of orthodontic templates will be presented. Such orthodontic templates may be used as a carrier system and/or as a bracket/base transfer tray that inserts into the carrier system. The carrier system is comprised of a generic carrier and individual bracket fixtures housed by the carrier and can either house bracket bases, brackets, or both. The bracket fixture references tooth digital models and locates patient tooth geometry (as discussed with reference to FIG. 1), which is obtained by using 3D capture and mapping technology such as video imaging, scanning, and ultrasound to create electronic tooth data. Bracket electronic data can either be scanned or created electronically to combine bracket and tooth electronic data. Additional factors of template design include, but are not limited to, material characteristics of the template (e.g., tear strength, peel strength), undercuts, and design features (e.g., singular template or compound template).

The tooth bracket trays may contain multiple or individual brackets for placement and bonding. The tooth bracket trays fit into the generic carrier allowing flexibility to use generic brackets while still referencing relative to tooth topology. The tooth bracket can be inserted into the generic bracket carrier using either a male or female engagement or locking mechanism. The bracket carrier may contain a 3D window, which allows specific tooth bracket and bracket base trays to be inserted. Additionally, the carrier can have the brackets imbedded in the carrier without a window.

The tooth bracket tray is created to fit over individual or multiple teeth using the digital tooth model and a method of creating a physical fixture from the data. The bracket tray can locate using individual or multiple teeth on the crown in the occlusal, lingual, or labial areas on the tooth. The purpose of the carrier is a global fixture for holding the bracket/base trays. The purpose of the trays is to provide proper bracket and base location on the tooth surfaces during positioning and bond curing. By providing occlusal and labial references from multiple teeth, the bracket is able to rest in the patient's mouth without additional fixtures and engage the bracket base to the tooth surface.

The bracket trays would be created either directly from the tooth data using numerically controlled manufacturing or rapid prototyping methods such as NC machining or stereo-lithography or indirectly using a male model of the teeth and brackets created by NC controlled methods as mentioned above and vacuum-forming or another process to create a fixture from the physical tooth and bracket model. The carrier and trays can be composite or clear material to allow UV curing of adhesives through the fixture. Additionally, an NC robot can place brackets into the bracket tray using 3D tooth and bracket data.

The carrier system and trays can have a capillary or "reservoir" system so that the excess bond material can fill into this area when pressure is applied to the fixture during tooth engagement. This prevents excess bond material from building up between the bracket and the tooth, allowing more accurate placement and less variability in the overall bonding process. In addition, fiber optics may be added to the carrier such that light may be used to cure the brackets.

In addition, the orthodontic template may be generated as a bracket tray using a male tooth model with representation of the brackets in the model. The male tooth model with bracket representation is created referencing 3D tooth data and 3D bracket data using 3D capture and mapping technology such as video imaging, scanning, and ultrasound. The bracket data can be either scanned in using above-described technologies or generated directly within the 3D data from published profiles. The female tray (impression) is created using vacuum-forming or other techniques for creating a fixture from a physical male model. Alternatively, the female tray may be created directly by using 3D tooth and bracket data and utilizing NC machining or stereo-lithography techniques.

Further, the carrier system and trays can provide direct environments for optimal bonding. The carrier can provide either suction or dispersion to the teeth through a series of capillaries throughout the fixture. The capillaries act as fluid channels to provide either suction of air and liquid or dispersion of air and liquid to and from the teeth. Relevant liquid may include but not be limited to primers, adhesives, sealants, water, and saliva.

Still further, a custom bracket bases may be created using 3D tooth data contoured to fit the patient's teeth. This concept involves creating bracket bases individually, which can have custom surfaces on the tooth side and the bracket side, and permanently installing them on the patient's teeth and interlocking the bracket to the base after bonding the base. Tooth geometry is provided by using 3D capture and mapping technology such as video imaging, scanning, and ultrasound. A base carrier fixture can be created to hold custom bases during base installation and can also be created referencing 3D tooth data. Custom bases can contain specific features to provide an adhesive "reservoir" inset into the base for uniformity of bond thickness and strength and increase post bonding positional accuracy. The base tray allows the bases to be installed in the patient's mouth and the brackets subsequently bonded to the base. The base tray can reference either individual or multiple teeth and can place one or more bases at a time. The base tray can also be composite or made of transparent materials to allow UV light to pass through for adhesive curing.

Yet further, bracket placement verification can be provided at any step of orthodontic treatment using the 3D capture and mapping technology. Additional techniques such as non-destructive testing can be used to verify bond strength of the bracket bond on each tooth.

In addition, an orthodontic bracket without a base may be replaced with a unique adhesive bonding surface. The bracket and tooth will have individual bond layers and the bracket base will not be present. An interlocking mechanism or other interface is attached to both the tooth and the bracket individually to allow engagement and disengagement of the bracket to the base during bracket installation. By separating the pad and the bracket, the pad is allowed more flexibility in terms compensating for adhesive thickness, materials, and surface characteristics of both sides of the bracket base. Both the pad and bracket location can be verified using the 3D capture and mapping technology. As such, only the pad could be sent to the orthodontist or a pre-bonded bracket may be sent.

Still further, shaping of the bracket adhesive to the tooth configuration may be done to improve bonding and location. This can be provided by removing excess adhesive and cutting to a specific adhesive footprint shape through conventional or machine cutting techniques prior to installation. An additional method for custom adhesive shaping is to "grow" or deposit material using NC, deposition, or rapid prototyping techniques referencing 3D tooth and bracket data. The adhesive perform is cut or deposited to a specific shape based on 3D tooth data. Due to current curing techniques of the adhesive on the bracket, this requires a UV resistant package for transporting the bracket.

As such, the any one of the following benefits, among others, are obtained singularly or in combination:
(1) Quicker and more accurate placement of brackets due to fixture single or multiple tooth references created from accurate 3D tooth data.
(2) Improved bond strength and improved accuracy provided by custom bases and adhesive shaping based on accurate 3D tooth data. The bases, the bonding agent, and adhesive pads may be shaped to the tooth topology using the 3D tooth data.
(3) Electronic generation and data representation of both patient's teeth and orthodontic brackets.
(4) Adhesive reservoir provided on the base or bracket to provide uniform bond thickness and strength.
(5) Adhesive reservoir on bracket/base tray and carrier to allow bond material runoff to provide uniform bond thickness and improve positional location.
(6) Bracket placement validation during any step using 3D scanning. Verification of bond strength of brackets and bases using non-destructive testing technology.
(7) Closed loop real-time location feedback system during bracket positioning.
(8) Transparent carrier and bracket/base tray material for UV or laser curing of bonding agents.
(9) Bases are bonded to the patient's tooth or teeth either independently or using a carrier/base tray without placing brackets. Brackets are connected to bases with an interlock method.
(10) UV resistant transporting package may be used.
(11) Elimination of bracket base using and interlocking bracket and tooth for attachment method. The locking mechanism is individually bonded to both the tooth and the bracket.
(12) The carrier contains a 3D window that allows specific tooth bracket trays to be inserted.
(13) The bracket tray may contain multiple or individual brackets for placement and bonding and references single or multiple tooth geometry from electronic tooth data.
(14) Placement of brackets in the bracket tray using a NC robot referencing 3D tooth and bracket data or a stereo lithographic model.
(15) The carrier may also be windowless and have the bracket impression imbedded in the carrier. The brackets can be inserted manually or through NC controlled robotics.
(16) The carrier and bracket tray can have a capillary system which can remove and supply gases and liquids such as sealant, primers, and water suction to provide an improved environment for bracket location and bonding.
(17) Female bracket tray using a male tooth model with actual or simulated brackets in place can be used.
(18) Male tooth model created from 3D tooth and bracket data can be used.
(19) Female bracket tray created using 3D tooth and bracket data.
(20) The orthodontist may be provided a mold of the orthodontic structure with the orthodontic apparatus installed such that he/she may create a template.
(21) Can control undercuts prior to placement of the brackets into the template.

Figure 8:
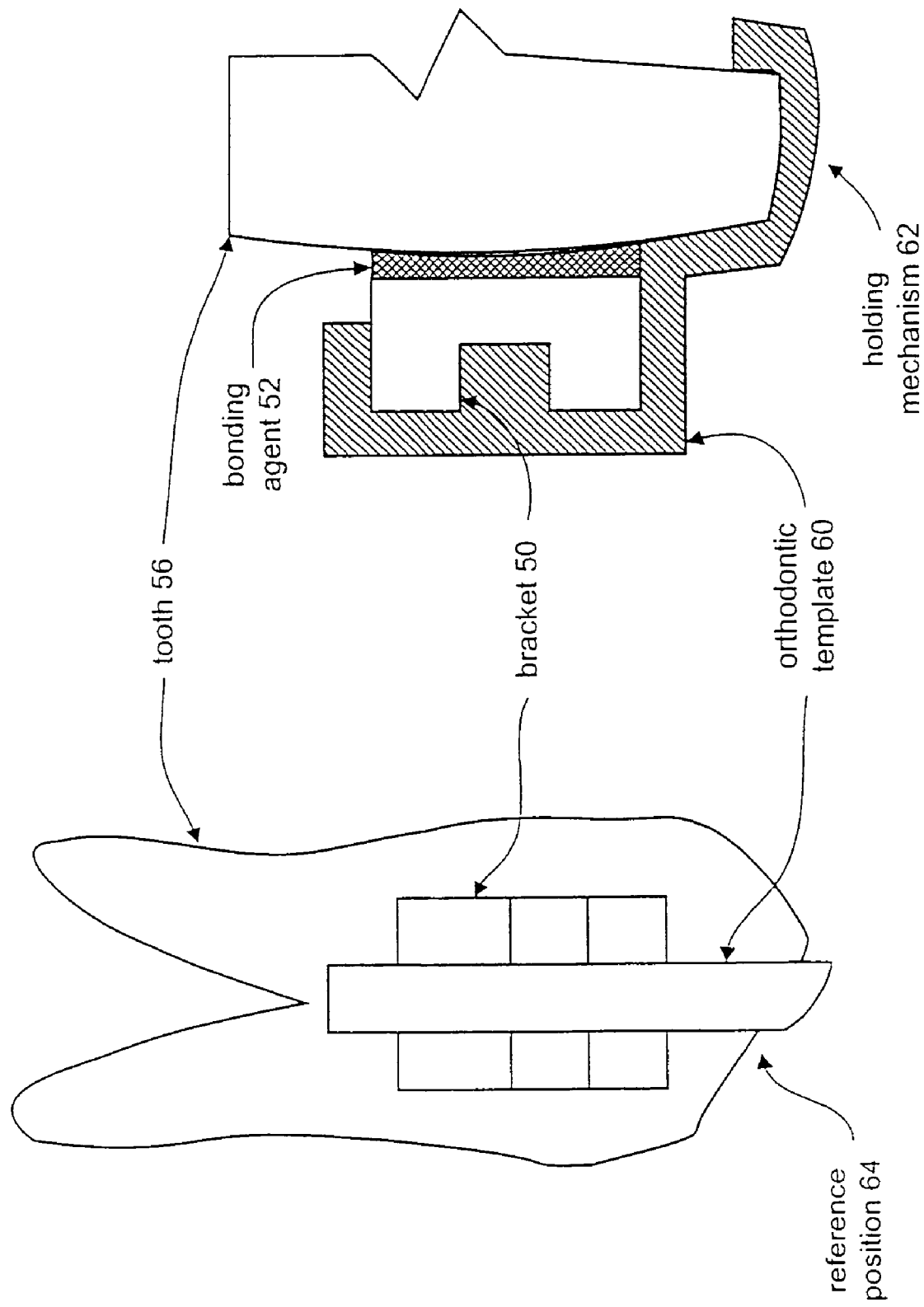
FIG. 8 illustrates a graphical representation of a orthodontic template in accordance with the present invention.

FIG. 8 illustrates a graphical representation of one particular orthodontic template 60. In this illustration, the tooth has the bracket 50 ready to be bonded thereto by the bonding agent 52. The orthodontic template 60 has a receptacle for holding the bracket in place and a corresponding holding mechanism 62 that corresponds to a reference position 64 on the tooth. As such by having the digital image of the tooth, the properties of the tooth, i.e., contour shape, unique geometries, etc. is digitally known. Utilizing this information as a reference position 64 for the orthodontic template, the holding mechanism 62 may be readily derived. By having the holding mechanism 62 of the orthodontic template 60 customized to the reference position 64 of a given tooth (i.e., the unique shape of the tooth or a portion thereof), the bracket can be accurately positioned in accordance with the digital modeling of bracket placement.

Figure 9:
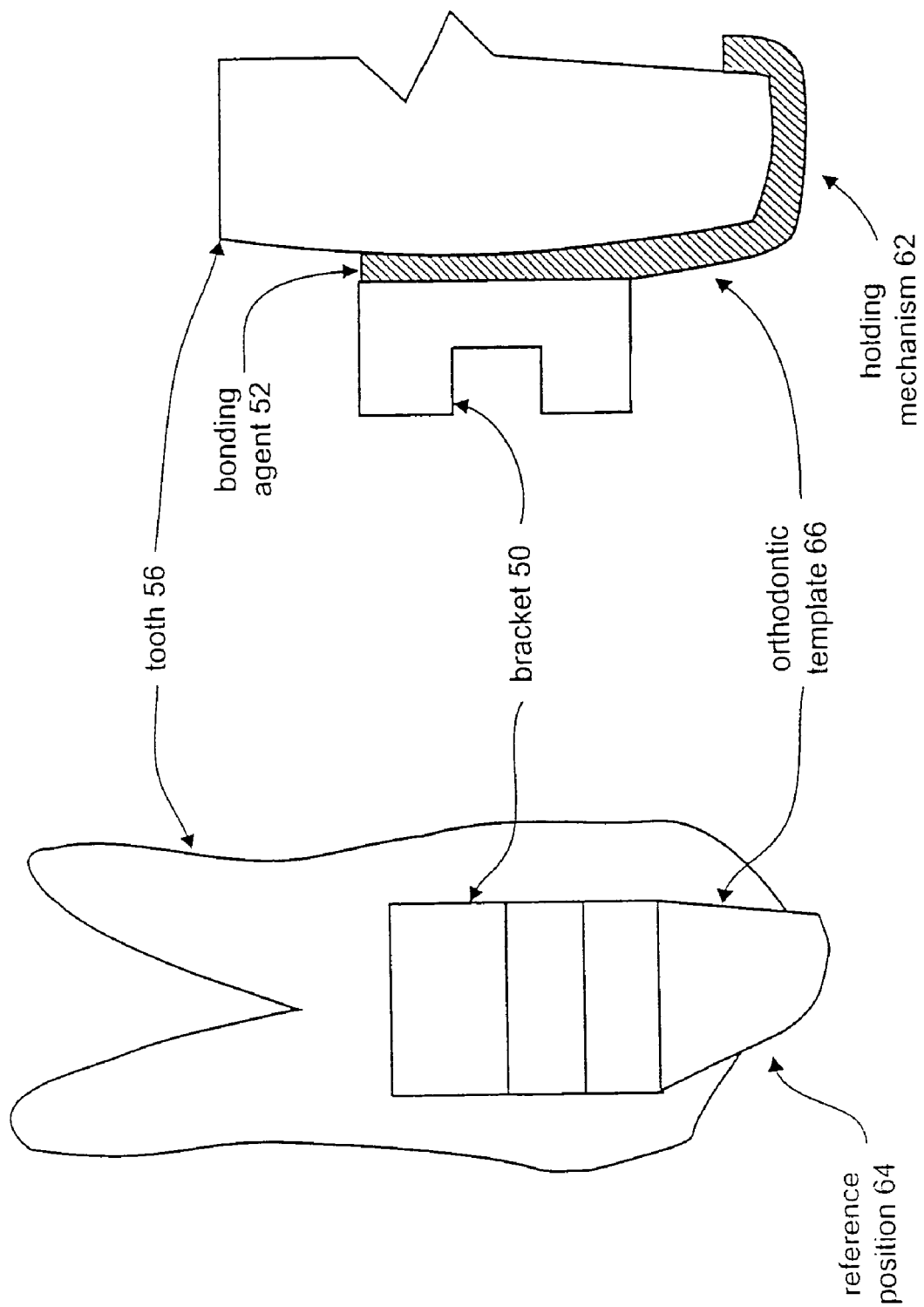
FIG. 9 illustrates a graphical representation of an alternate orthodontic template in accordance with the present invention.

FIG. 9 illustrates an alternate orthodontic template 66. In this embodiment of an orthodontic template 66, the bonding agent 52 is extended to produce the orthodontic template 66. The bonding agent includes a holding mechanism 62 that corresponds to the referenced position 64 of the given tooth 56. In this embodiment, once the bracket is positioned, the bonding agent is activated to adhere the bracket to the tooth and the excess bonding agent is removed. As such, no additional parts are required as in the example of FIG. 8.

Figure 10:
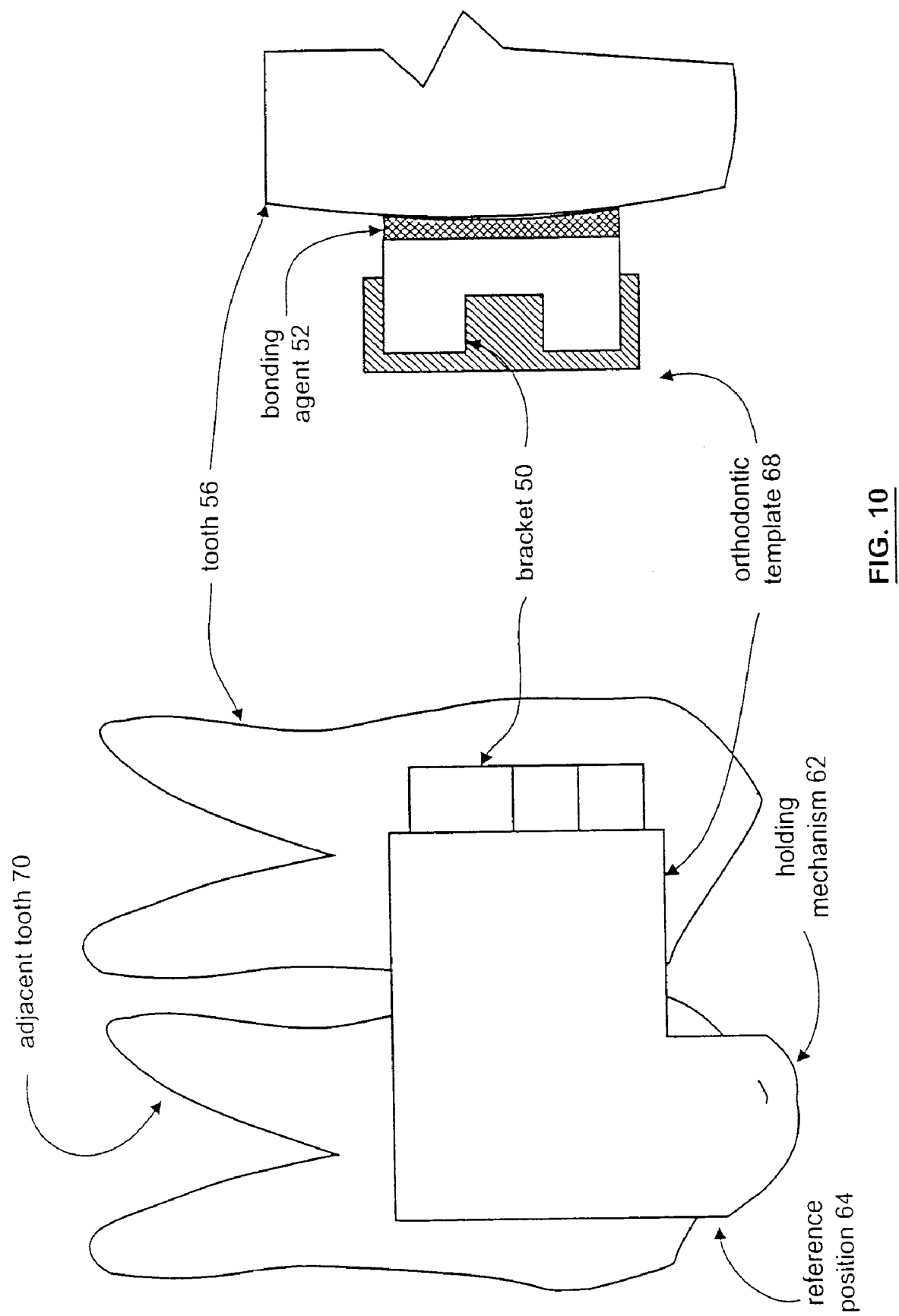
FIG. 10 illustrates a graphical representation of another orthodontic template in accordance with the present invention.

FIG. 10 illustrates another embodiment of an orthodontic template 68. In this embodiment, the referenced position 64 is on an adjacent tooth 70. The holding mechanism 62 of orthodontic template 68 is then designed in accordance with the reference position 64 of the adjacent tooth. Note that the adjacent tooth may be a tooth with or without a bracket already mounted. As such, an orthodontist may utilize a plurality of dependent orthodontic templates to position brackets on a patient's teeth in a sequential manner. For example, one tooth may be selected as a primary tooth that is to be the first tooth to have a bracket mounted thereon. Accordingly, the orthodontic template for the primary tooth would have a reference position that did not include a previously placed bracket. Subsequent bracket placement may include orthodontic templates that have the reference position being the placement of the bracket on the primary tooth.

Figure 11:
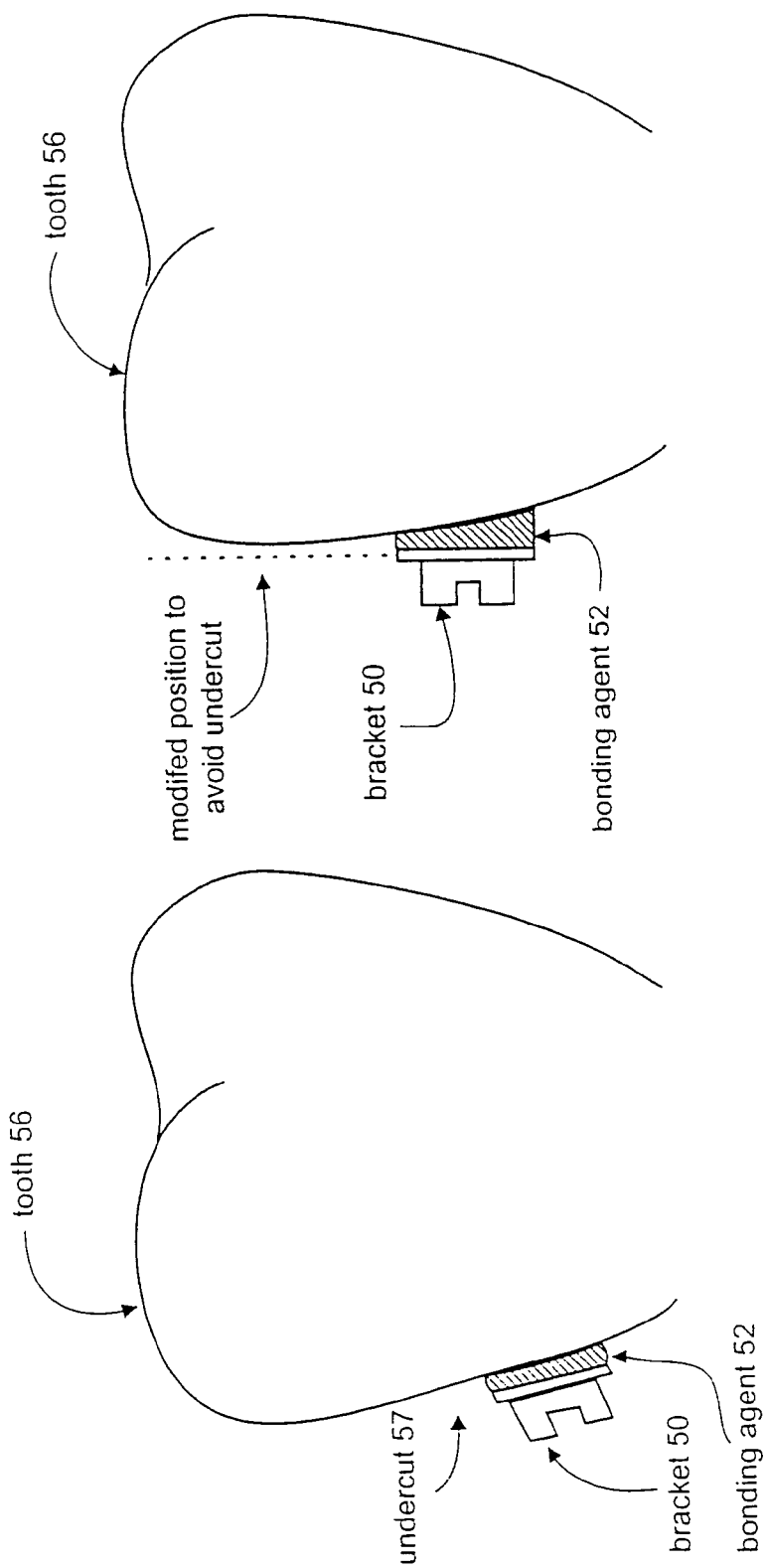
FIG. 11 illustrates a graphical representation of bracket undercut correction in accordance with the present invention.

FIG. 11 illustrates a graphical representation of a correction for an undercut condition. As is known, when the bracket 50 is placed on the tooth 56 such that a vertical line from the bracket intersects with the tooth 56, an undercut 57 condition exists. When an undercut 57 condition exists, it is difficult to install the bracket using a transfer tray, since, when the transfer tray is removed after the bracket as been bonded, it must be pulled off at an angle. By pulling the tray off at an angle, there is a risk of loosing, or pulling off, the bracket 50. To avoid the undercut 57 condition, the bonding agent thickness may be varied to provide the same force system as the bracket placement with the undercut 57. However, by modifying the position of the bracket, the undercut condition is avoided as are the associated difficulties.

Figure 12:
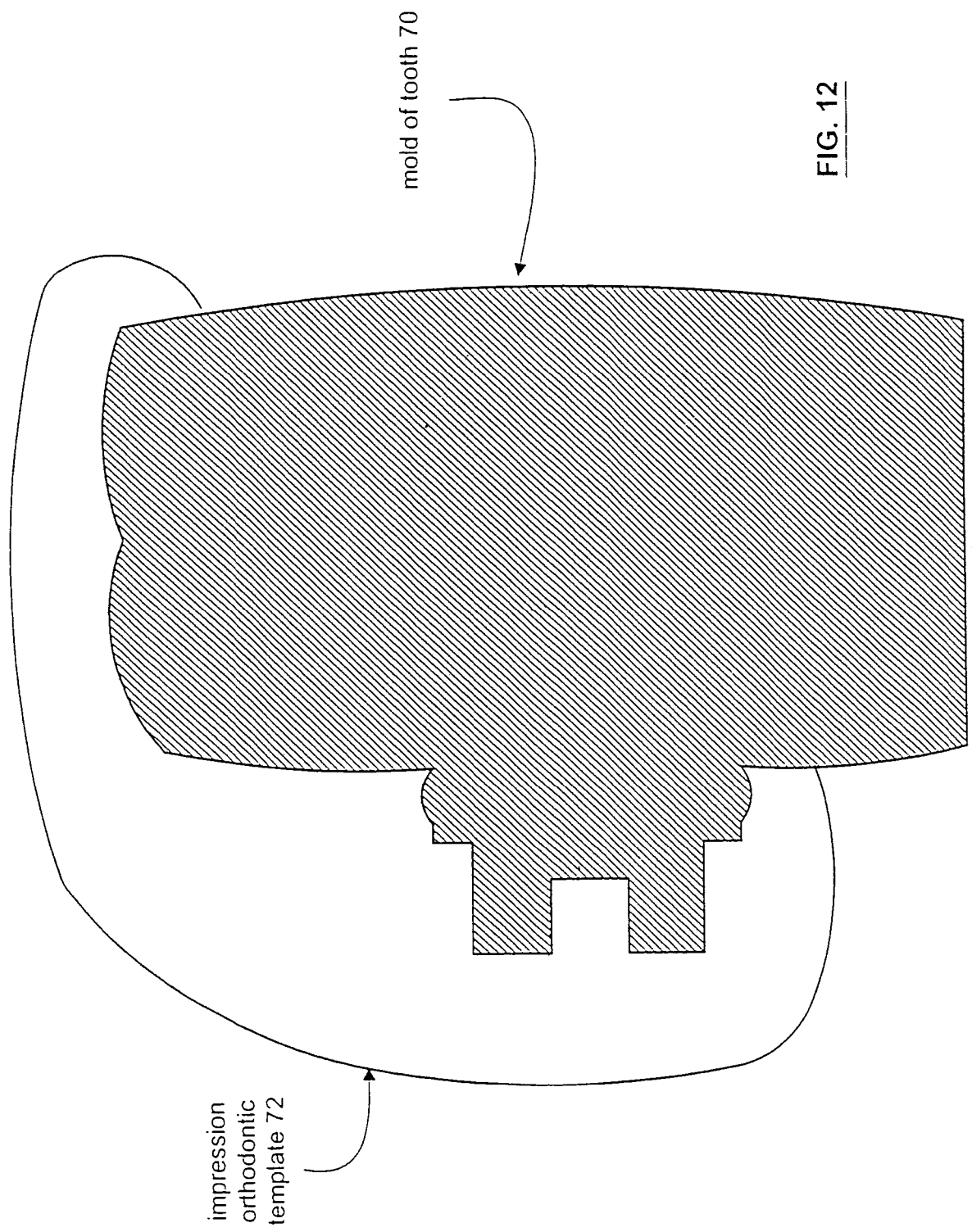
FIG. 12 illustrates a graphical representation of a tooth mold and an over-mold orthodontic template in accordance with the present invention.

FIG. 12 illustrates a graphical representation of a positive mold of a tooth 70 being fabricated from the digital image of the orthodontic structure with the orthodontic apparatus installed. Note that the orthodontic apparatus includes at least one of brackets, rapid maxillary expansion device, retainer, arch wire, bands, appliances, bonding pad, bonding agent physical properties, bonding agent adhering properties, and headgear tubes. As such, a portion of the selected orthodontic apparatus may be any one of these elements. For example, if the digital model were made with the brackets installed with a bonding agent, the positive mold would include the bracket positioning in the ideal location, along with the ideal bonding agent properties. The bonding agent properties include adherence properties (e.g., bonding strength), physical properties (e.g., height, width, depth), and type of bonding agent (e.g., UV cured, laser cured, chemical cured).

The positive mold 70 may be for a single tooth or for any number of teeth and be shipped as the orthodontic template to an orthodontist. As such, the orthodontist may fabricate the over-mold or impression orthodontic template for holding and positioning the portion of the selected orthodontic apparatus, i.e., the brackets, wires, etc. Alternatively, the over-mold may be fabricated along with the mold 70, where the combination is provided to the orthodontist as the orthodontic template.

Figure 15:
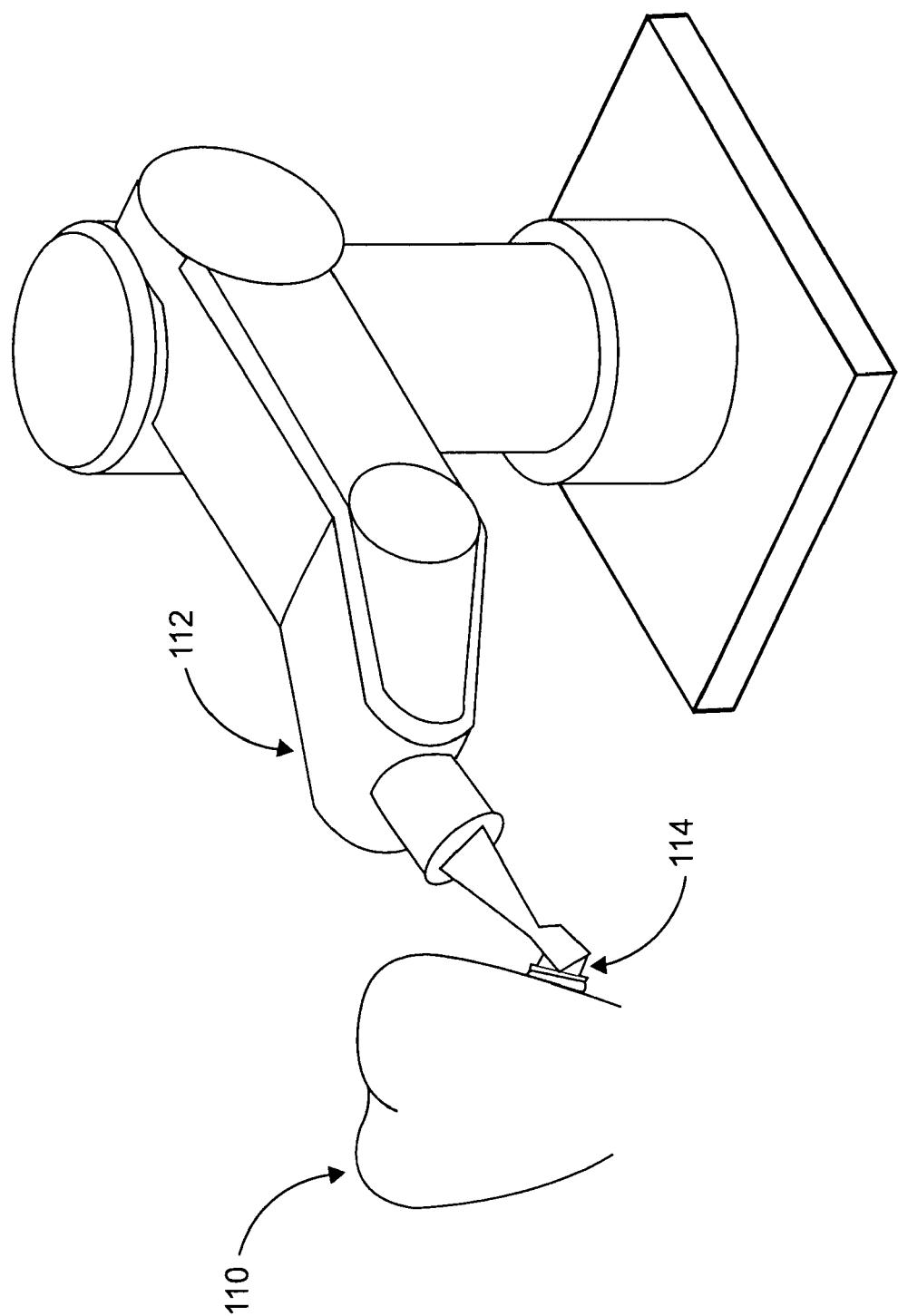
FIG. 15 illustrates a robot placing a bracket on a physical model of a tooth.

As an alternative to fabricating the mold 70 shown in FIG. 12 with the orthodontic apparatus as part of the mold, a mold of the orthodontic structure, without brackets, may be made. As shown in FIG. 15 from the mold 110, a robot 112, or electronic feedback mechanism may be used to place actual bracket 114 on the mold. Once this is done, the over-mold may be fabricated.

Figure 13:
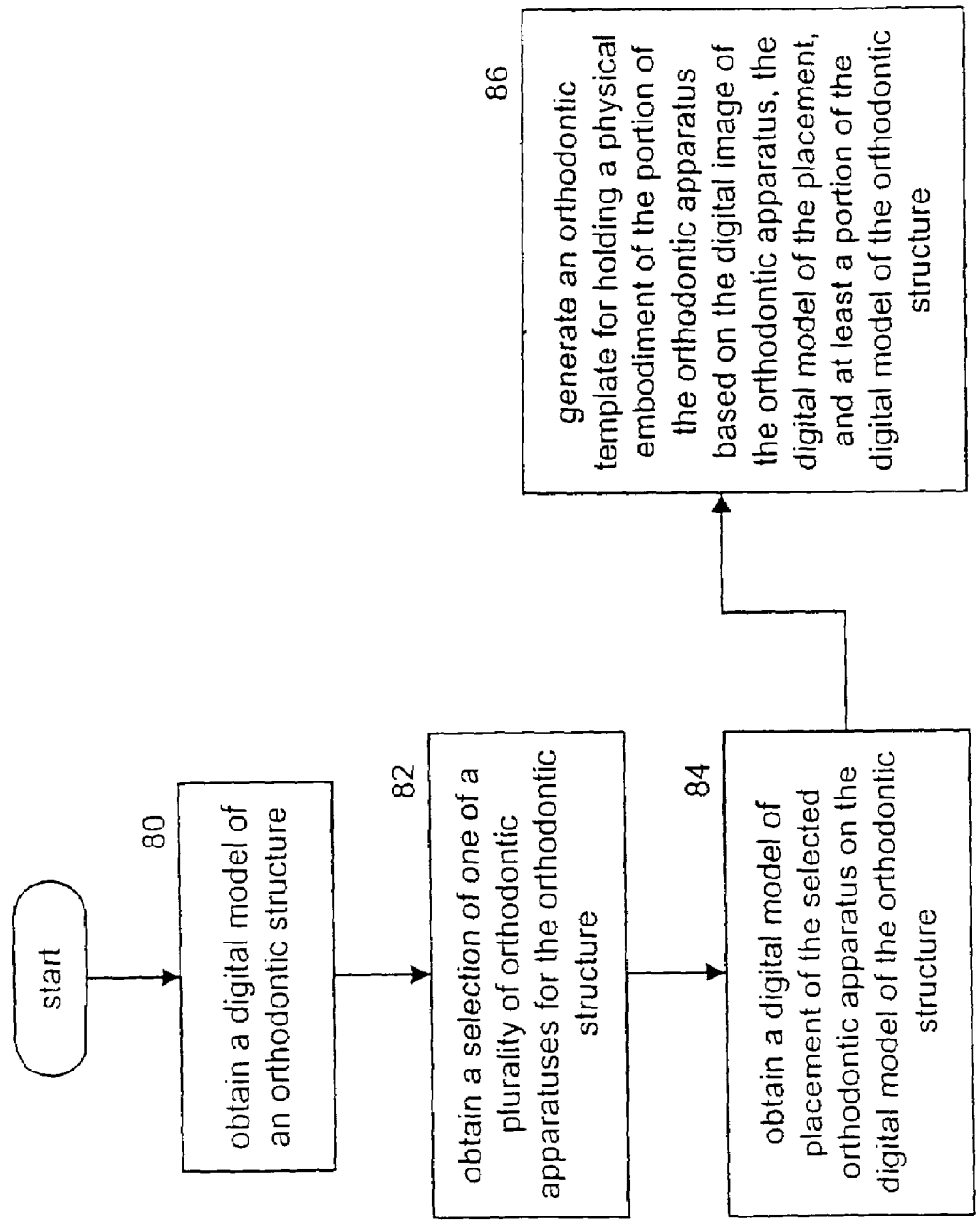
FIG. 13 illustrates a logic diagram of a method for generating a orthodontic template in accordance with the present invention.

FIG. 13 illustrates a logic diagram of a method for generating an orthodontic template that assists in the placement of an orthodontic apparatus. The process begins at step 80 where a digital model of an orthodontic structure is obtained. This has been previously discussed and has been referenced to a patent application having a Ser. No. of 09/451,637, now U.S. Pat. No. 6,471,512. Note that the digital model of the orthodontic structure may be obtained by directly scanning the orthodontic structure of the orthodontic patient to obtain image data and then converting the image data into the digital model. The process then proceeds to step 82 where a selection of one of a plurality of orthodontic apparatuses is obtained for the given orthodontic structure. As previously mentioned, the database 24 may include a plurality of orthodontic appliances that the orthodontist may use to select the given apparatus to be used on a given patient. In addition, an orthodontic site system may select the digital image of the orthodontic apparatus from the database of digital representations of the orthodontic apparatuses. Having done this, the digital images would then be provided to the orthodontic server. Note that the orthodontic site system may be operated by the orthodontist and/or an employee of an orthodontist. Further note that the orthodontic apparatus may include active or passive orthodontic appliance such as brackets, rapid maxillary expansion devices, retainers, arch wires, bands, appliances, and/or head gear tubes.

The process then proceeds to step 84 where a digital model of the placement of the selected orthodontic apparatus on the digital model on the orthodontic structure is obtained. This process may be achieved utilizing the processing described in application previously mentioned having a Ser. No. of 09/451,609, now U.S. Pat. No. 6,250,918. The process then proceeds to step 86 where a digital model of a tooth mounting apparatus for a given tooth is retrieved. For example, if a bracket is to be mounted on a tooth as determined in step 84, the digital model for that bracket is obtained for the given tooth. The process then proceeds to step 88 where an orthodontic template for holding a physical embodiment of the tooth mounting apparatus is generated based on the digital image of the tooth mounting apparatus, the digital model of the placement, and at least a portion of the digital model of the orthodontic structure.

The orthodontic template may be fabricated by producing, as the orthodontic template, a physical model of the orthodontic structure with the at least a portion of the selected orthodontic apparatus placed thereon from the digital model of placement of the selected orthodontic apparatus on the digital model of the orthodontic structure. Alternatively, the orthodontic template may be generated by producing, as part of the orthodontic template, an over-mold from the physical model of the orthodontic structure with the at least a portion of the selected orthodontic apparatus placed thereon; and installing physical embodiments of the at least a portion of the selected orthodontic apparatus into the over-mold.

As another alternative, the orthodontic template may be generated by producing a physical model of the orthodontic structure from the digital model of the orthodontic structure; and automatically placing the at least a portion of the selected orthodontic apparatus on the physical model of the orthodontic structure based on the digital model of placement of the selected orthodontic apparatus on the digital model of the orthodontic structure. From this process, the generation of the orthodontic template may further include producing, as part of the orthodontic template, an over-mold from the physical model of the orthodontic structure with the at least a portion of the selected orthodontic apparatus placed thereon; and installing physical embodiments of the at least a portion of the selected orthodontic apparatus into the over-mold. As an alternative additional processing, the generation of the orthodontic template may further include producing, as part of the orthodontic template, an over-mold from the physical model of the orthodontic structure with the at least a portion of the selected orthodontic apparatus placed thereon; and removing the over-mold from the physical model such that the at least a portion of the selected orthodontic apparatus is contained in the over-mold, wherein the automatic placement of the at least a portion of the selected orthodontic apparatus on the physical model of the orthodontic structure utilized a temporary bonding agent.

As yet another alternative to generating the orthodontic template, the orthodontic template may be generated by producing a mold of the placement of the at least a portion of the orthodontic apparatus on the orthodontic structure based on the digital model of the placement of the at least a portion of the orthodontic apparatus on the orthodontic structure, wherein the mold includes alignment structure corresponding to at least a portion of the orthodontic apparatus, and wherein the alignment structure aligns the at least a portion of the orthodontic apparatus for installation. The alignment structure may be location windows and/or alignment guides. Further, the alignment structure may be used to place the brackets on a mold of the patient's teeth. The mold with the brackets mounted thereon may then have an impression taken to obtain the template.

As still another alternative to generating the orthodontic template, the orthodontic template may be generated by generating a first orthodontic template for a first orthodontic appliance of the at least a portion of the selected orthodontic apparatus, wherein the first orthodontic appliance corresponds to a first tooth of the orthodontic structure; and generating a second orthodontic template for a set orthodontic appliances of the at least a portion of the selected orthodontic apparatus, wherein the set orthodontic appliance corresponds to a set of teeth of the orthodontic structure.

Once the orthodontic template is designed, it may be fabricated in accordance with the digital image for the orthodontic template. Accordingly the digital image for the orthodontic template may include programming instructions for milling, machining, 3D printing, and/or generating a mold to produce the orthodontic template. Once the orthodontic template has been produced, a physical embodiment of the bracket is installed therein and delivered to the orthodontist for installation. Once the orthodontic template is positioned on the tooth, the orthodontic template may be scanned to verify proper positioning and repositioned if necessary. If the orthodontic template is properly positioned, the bracket is bonded to the tooth. The bracket positioning may also be scanned to determine that the bracket is positioned in the desired location.

Figure 14:
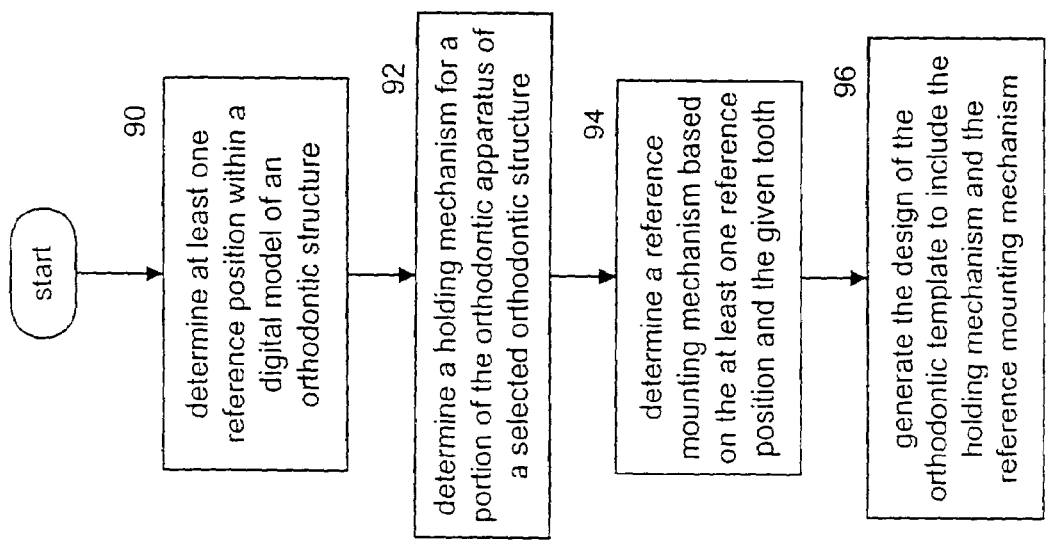
FIG. 14 illustrates a logic diagram of an alternate method for generating a orthodontic template in accordance with the present invention.

FIG. 14 illustrates a logic diagram of a method for generating a orthodontic template that assists in placement of an orthodontic apparatus. The process begins at step 90 where at least one referenced position within a digital model of an orthodontic structure is determined. Note that the at least one referenced position may be a bracket on an adjacent tooth, an opposing tooth, a plurality of teeth, a plurality of brackets, and/or the given tooth itself. The process then proceeds to step 92 where a holding mechanism for a tooth mounting apparatus of a selected orthodontic structure is determined. The process then proceeds to step 94 where a referenced mounting mechanism based on the at least one reference position for the given tooth is determined. The process then proceeds to step 96 where the design of the orthodontic template is generated to include the holding mechanism and the referenced mounting mechanism. Note that if the referenced position is chosen to be the given tooth, the design of the orthodontic template includes the holding mechanism in accordance with the surface geometry of the given tooth. Alternatively, if the referenced position is an adjacent tooth, the orthodontic template is designed to include the holding mechanism in accordance with the surface geometry of the adjacent tooth. Further note that the material used to generate the orthodontic template may be the bonding agent. Alternatively, the tooth mounting apparatus may be fabricated to include the orthodontic template as an extension of the tooth mounting apparatus, wherein the orthodontic template is fabricated as a detachable placement wire.

Figure 16:
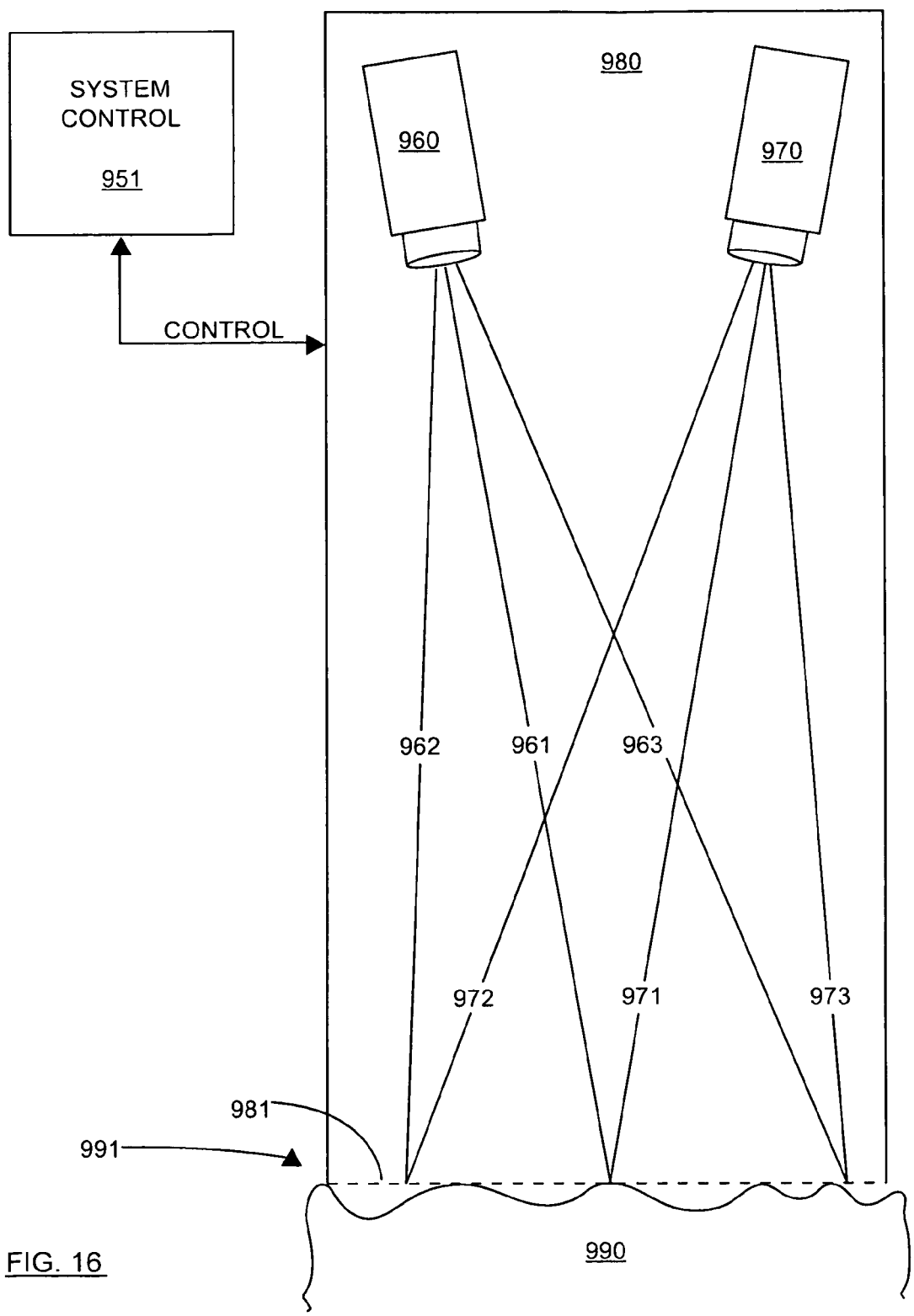
FIG. 16 illustrates a scanning device.

FIG. 16 illustrates a system controller 951 that provides control signals to the scanning device 980. The scanning device 980 projects an image bound by lines 962 and 963, and retrieves, or views, the images within the reflected lines 972 and 973. In one operation, the system controller 951 provides specific information to the scanner 980 specifying a specific image to be projected upon the surface 991 of the object 990. The reflected image is captured by the scanning device 980, which in turn provides the captured information back to the system controller 951. The captured information can be provided back to system controller 951 automatically, or can be stored within the scanning device 980 and retrieved by the system 951. The image data once received by the system controller 951 is analyzed in order to determine the shape of the surface 991. Note that the analysis of the received data can be performed either by the system controller 951, or by an external-processing device that is not shown. Further illustrated in FIG. 16 is the scanning device 980, which includes a projecting device (projector) 960 and a viewing device (viewer) 970. The projector 960 is oriented such that the image is projected on the object 990. The projector 960 has a projection axis 961. The projection axis 961 begins at the center of the lens projecting the image and is representative of the direction of projection. Likewise, the viewer 970 has a view axis 971 that extends from the center of the lens associated with the viewer 970 and represents the direction from which images are being received.

The illustrations provided thus far have related to a single orthodontic template corresponding to a single bracket. The teachings already described are equally applicable to generating multiple orthodontic templates for multiple bracket placements sequentially and/or for generating a single orthodontic template that places multiple brackets simultaneously. To achieve this, a digital image for each corresponding bracket for a set of teeth of the orthodontic structure is retrieved. Having done this, a orthodontic template for holding a physical embodiment of each of the corresponding brackets is determined based on the digital image of the corresponding brackets, the digital model of the placement, and at least a portion of the digital image of the orthodontic structure. As mentioned, the orthodontic template may be fabricated as a single structure for parallel installations of the brackets, or generated as a orthodontic template having segregatable structures for individual installation of the corresponding brackets.

Using an iterative method in accordance with the present invention is advantageous over prior methods that were ultimately based upon a single two-dimensional analysis. By using a three-dimensional model in accordance with a specific embodiment of the present invention in conjunction with an iterative process, any factor that effects tooth movement (i.e. brackets, wires, adhesion, physiological changes) can be simulated to determine appropriate treatment changes. Such compensation in treatment is not possible using prior methods which were based upon assumptions from a single model that the tooth movement would progress in a known manner. Therefore, the prior art methods would specify and a single static treatment based upon this assumption. If any unwanted tooth movement occurred during treatment, the specified treatment would no longer be valid, requiring changes to be made based upon a practitioner's expertise. The present system provides a dynamic system that through the use of periodic feedback, i.e. periodic three-dimensional scanning, can be monitored and adjusted as needed by the system in an efficient manner. As such, unexpected tooth movement, such as occurs when a patient does not cooperate, or through biological changes, can be readily controlled.

The preceding discussion has presented a method and apparatus for fabricating a orthodontic template. By utilizing digital imagery and digital models, a orthodontic template may be fabricated without the bracket being the focal point of orthodontic treatment. By removing the focal point from the bracket, more flexible orthodontic treatment may be obtained. The orthodontic template produced in accordance with the teachings of the present application assist in such orthodontic treatment. As one of average skill in the art will appreciate, other embodiments may be derived from the teachings of the present patent without deviating from the scope of the claims.

What is claimed is:

1. A method for generating an orthodontic template that assists in placement of one or more orthodontic brackets on the orthodontic structure of a patient, the method comprises the steps of:
   a) simulating tooth movement in a digital model of orthodontic structure of a patient thereby obtaining a digital model of placement; wherein said digital model of placement comprises digital models of said one or more selected orthodontic brackets placed upon said digital model of said orthodontic structure for providing desired tooth movement;
   b) producing a physical model of placement by placing the physical embodiment of each of the one or more selected orthodontic brackets onto the physical model of the orthodontic structure using a robot in accordance with said digital model of placement; and
   c) generating an orthodontic template using said physical model of placement.

2. The method of claim 1, wherein the physical model of the orthodontic structure is obtained from the orthodontic structure of the patient.

3. The method of claim 1, wherein the one or more selected orthodontic brackets are selected from a database of digital representations of the orthodontic brackets.

4. The method of claim 1, wherein the physical embodiment of each of the selected one or more orthodontic brackets has adhesive on the base and wherein the adhesive is cured after placement of the brackets on the orthodontic structure.

5. The method of claim 4, wherein the adhesive on the base is in the form of a customized bonding pad.

6. The method of claim 1, wherein the step of generating the orthodontic template comprises the steps of producing an over-mold from the physical model of placement and then removing the over-mold from the physical model of placement.

7. The method of claim 6, wherein the physical embodiment of each of the selected one or more orthodontic brackets are inserted in the over-mold.

8. The method of claim 7, wherein the physical embodiment of each of the selected one or more orthodontic brackets are inserted in the over-mold by a device wherein said device is either said robot or another robot.

9. The method of claim 6, wherein the step of removing the over-mold from the physical model is performed such that the physical embodiment of each of the one or more selected orthodontic brackets is contained in the over-mold, wherein the automatic placement of the physical embodiment of each of the one or more selected orthodontic brackets on the physical model of the orthodontic structure utilized a temporary bonding agent.

10. The method of claim 1, wherein the orthodontic template is generated by a vacuum-forming process using the physical model of placement and subsequently inserting the physical embodiment of each of the selected one or more orthodontic brackets in the orthodontic template.

11. The method of claim 1, wherein the orthodontic template is generated for either the upper arch or the lower arch or both arches.

12. The method of claim 1, wherein the orthodontic template is made of transparent material enabling UV or laser curing of the bonding agents.

13. The method of claim 1, wherein the digital model of placement is determined using the orthodontic treatment planning computer software instructions.

14. An apparatus for generating an orthodontic template that assists in placement of one or more orthodontic brackets, the apparatus comprising:
   a server comprising a processing module and memory; wherein said processing module performs processing steps via operational instructions stored in said memory thereby simulating tooth movement in a digital model of orthodontic structure of a patient thereby obtaining a digital model of placement; said memory storing said digital model of placement; wherein said digital model of placement comprises digital models of one or more selected orthodontic brackets placed upon a digital model of orthodontic structure;
   a robot capable of producing a physical model of placement by placing a physical embodiment of each of the selected one or more orthodontic brackets onto a physical model of the orthodontic structure in accordance with the digital model of placement; and
   a vacuum-forming machine for generating the orthodontic template using the physical model of placement.

15. The apparatus of claim 14, further comprising a scanner for producing the digital model of the orthodontic structure.

16. The apparatus of claim 14, wherein the memory stores a database of digital representations of a plurality of orthodontic brackets.

17. The apparatus of claim 16, wherein the memory stores further operational instructions that cause the processing module to:
   a) obtain a digital model of an orthodontic structure of an orthodontic patient; and
   b) obtain a selection of one or more orthodontic brackets for the orthodontic structure.

18. The apparatus of claim 14, further comprising an UV device for curing the adhesive on the back of the orthodontic brackets.

19. The apparatus of claim 14, wherein the physical model of the orthodontic structure is obtained from the orthodontic structure of the patient.

20. The apparatus of claim 14, wherein the one or more selected orthodontic brackets are selected from a database of digital representations of the orthodontic brackets.

21. The apparatus of claim 14, wherein the physical embodiment of each of the selected one or more orthodontic brackets has adhesive on the base and wherein the adhesive is cured after placement of the brackets on the orthodontic structure.

22. The apparatus of claim 21, wherein the adhesive on the base is in the form of a customized bonding pad.

23. The apparatus of claim 14, wherein the orthodontic template comprises an over-mold produced and then removed from the physical model of placement.

24. The apparatus of claim 23, wherein the physical embodiment of each of the one or more selected orthodontic brackets is contained in the over-mold, wherein the automatic placement of the physical embodiment of each of the one or more selected orthodontic brackets on the physical model of the orthodontic structure utilized a temporary bonding agent.

25. The apparatus of claim 23, wherein the physical embodiment of each of the selected one or more orthodontic brackets are inserted in the over-mold.

26. The apparatus of claim 25, wherein the physical embodiment of each of the selected one or more orthodontic brackets are inserted in the over-mold by a device wherein said device is either said robot or another robot.

27. The apparatus of claim 14, wherein the orthodontic template is generated for either the upper arch or the lower arch or both arches.

28. The apparatus of claim 14, wherein the orthodontic template is made of transparent material enabling UV or laser curing of the bonding agents.

29. The apparatus of claim 14, wherein the memory further stores orthodontic treatment planning instructions for determining said digital model of placement.

* * * * *